United States Patent [19]
Koide et al.

[11] Patent Number: 5,395,305
[45] Date of Patent: Mar. 7, 1995

[54] MULTILAYER WOUND COVERING MATERIALS COMPRISING A SUPPORTING LAYER AND A MOISTURE PERMEATION CONTROLLING LAYER AND METHOD FOR THEIR MANUFACTURE

[75] Inventors: Mikio Koide; Jun Konishi; Kazuhito Ikegami; Ken-ichi Osaki, all of Kanagawa, Japan

[73] Assignee: Terumo Kabushiki Kaisha, Tokyo, Japan

[21] Appl. No.: 745,889

[22] Filed: Aug. 16, 1991

[30] Foreign Application Priority Data

Aug. 30, 1990 [JP] Japan .................................. 2-226663
Sep. 19, 1990 [JP] Japan .................................. 2-247301

[51] Int. Cl.⁶ .............................................. A61F 13/00
[52] U.S. Cl. ........................................ 602/48; 602/58; 604/304
[58] Field of Search ................... 602/48, 49, 52, 58, 602/900; 604/304, 336; 424/445, 446, 447

[56] References Cited

U.S. PATENT DOCUMENTS

| | | | |
|---|---|---|---|
| 4,307,717 | 12/1981 | Hymes et al. | 604/304 |
| 4,393,048 | 7/1983 | Mason, Jr. et al. | 604/304 |
| 4,466,431 | 8/1984 | Tharrat et al. | 424/447 |
| 4,728,642 | 3/1988 | Pawelchak et al. | 602/48 |
| 4,738,257 | 4/1988 | Meyer et al. | 602/48 |
| 4,746,514 | 5/1988 | Warne | 602/49 |
| 4,773,409 | 9/1988 | Cilento et al. | 602/49 |
| 4,860,737 | 8/1989 | Lang et al. | 602/47 |
| 4,871,490 | 10/1989 | Rosiak et al. | 602/900 |
| 4,909,244 | 3/1990 | Quarfoot et al. | 128/156 |
| 4,977,892 | 12/1990 | Ewall | 128/156 |
| 5,035,893 | 7/1991 | Shioya et al. | 424/445 |
| 5,160,328 | 11/1992 | Cartmell et al. | 604/307 |

FOREIGN PATENT DOCUMENTS

| | | |
|---|---|---|
| 149998 | 7/1985 | European Pat. Off. . |
| 342950 | 11/1989 | European Pat. Off. . |
| 371736 | 6/1990 | European Pat. Off. . |
| 84/00111 | 1/1984 | WIPO . |

OTHER PUBLICATIONS

World Patents Index, accession No. 87-266570, week 38, Derwent Publications Ltd., and JP-A-62 183,760 (Terumo Corp.) Aug. 12, 1986.
World Patents Index, accession No. 91-359187, week 49, Derwent Publications Ltd., and JP-A-3,242,145 (Terumo Corp.) Oct. 29, 1991.

*Primary Examiner*—Randall L. Green
*Assistant Examiner*—Mary Beth Jones
*Attorney, Agent, or Firm*—Burns, Doane, Swecker & Mathis

[57] ABSTRACT

Wound-covering materials comprising two layers, a first support layer which is to be in contact with a wound and a second moisture permeation-controlling layer which may optionally contain an antimicrobial agent are taught. The support layer is formed from a biocompatible highly aqueous gel-forming substance, e.g., carboxymethylcelluloses, alginates, hyaluronates, poly(meth)acrylates, chitosan derivatives and chitin derivatives, and at least a portion of the support layer which is to be in contact with a wound is coated with a water-repellant substance, e.g., silicones, polyurethanes, styrene-butadiene-styrene block copolymers and polytetrafluoroethylenes. The moisture permeation controlling layer may, e.g., be formed from steam permeable resin films made of silicone or polyurethane elastomers. The resultant wound-covering materials inhibit infection and pain, maintain adequate water retention, and do not produce bioincompatibility responses when applied to the site of wounds.

1 Claim, 2 Drawing Sheets

MULTILAYER WOUND COVERING MATERIALS COMPRISING A SUPPORTING LAYER AND A MOISTURE PERMEATION CONTROLLING LAYER AND METHOD FOR THEIR MANUFACTURE

BACKGROUND OF THE INVENTION

1. Field of the Invention

This invention relates to wound-covering materials and a method for preparing the same. More particularly, it is concerned with wound-covering materials which are applied to a site of skin defect when the skin is defectively injured by a wound, a burn or the like, These wound-covering materials keep said site of the skin defect in a wet state, reduce pain and prevent microbial infection to facilitate regeneration of the epidermis.

2. Description of the Prior Art

The use of a dry dressing and wet dressing as a method and material for treating wounds including traumatic dermal wounds and wounds caused by removal of skin for dermatoplasty as well as wound associated with disease is known in the art. In the former, healing is achieved by maintaining the wounded site dry until a crust is formed. The latter is directed to creation of adequately wet circumstances to enable floating of the epidermal cells. It is recognized in the latter method that more rapid healing of the wound is accomplished, less dry necrosis is formed and a protective effect on the wound surface is produced.

It is pointed out, however, as to the use of a surgical drape, one of the wet dressing techniques, that there is retention of a large amount of exudate which is possibly reabsorbed through the wound surface, risk of infection is high and direct contact of the adhesive with the wound surface may be detrimental to healing of the wound. The drape is also apt to be separated from the wound surface. A drape having small projections attached to the surface to be in contact with the wound surface is available, however, it is difficult to remove.

In order to overcome these problems there have recently been made available covering materials using a biopolymer such as collagen, chitin or fibrin on the area that can be in contact with the wounded site or those in which a moisture-retaining ingredient is dispersed in the rubber base material in order to achieve close contact, non-adhesion and maintenance of a highly aqueous state. In addition, wound-covering materials previously proposed by us are available which comprise a biocompatible hydrogel-forming support layer (for example, of carboxymethyl-cellulose, alginate, hyaluronate or poly(meth)acrylate) in which at least a portion of the area to be in contact with the wounded site is coated with a water-repellent substance and a moisture permeation-adjusting layer which is formed on the side opposite to the area of said support layer to be in contact with the wounded site (Japanese Patent Application Laid-Open-to-Public No. 183760/1987). All of the above-cited materials have achieved their purpose to some extent.

Although the prior art wound covering materials as mentioned above are effective to some extent, there is a problem of physical property in use as a wound-covering material in that the material used in forming a biocompatible base layer in an area to be in contact with the wounded site is apt to undergo degradation or detachment. Furthermore, the materials from the degradation or the detachment may be recognized as a foreign matter with the risk of delaying healing of the wound. Further, although the moisture permeation-adjusting layer formed on the opposite side of the area of the support layer to be in contact with the wound is required to possess an adequate moisture-permeating capacity and a capacity of inhibiting microbial attack, a considerably limited scope of materials meet both of the requirements.

An object of the invention is therefore to provide wound-covering materials in which the presence of a highly aqueous layer assures the adequate retention of the exudate and good contact with but no adhesion to the wound surface and which the highly aqueous support layer in use is not easily decomposed or detached when contacted with the wound thereby facilitating healing of the wound, especially the regeneration of the epidermis to result in rapid therapy of the wound and, furthermore, in which the properties of the moisture permeation-controlling layer can be set considerably freely and a method for preparing the same.

SUMMARY OF THE INVENTION

The above mentioned object can be achieved by the wound-covering materials given below and the methods for preparing the same.

(1) A wound-covering material comprising a support layer formed of a film of a biocompatible highly aqueous gel-forming substance, at least a part of an area to be contacted with wound being coated with a water-repellent substance and a moisture permeation-controlling layer formed on said support layer on the side opposite to the area to be contacted with wound, and optionally, the support layer and/or the moisture permeation-controlling layer containing an antimicrobial agent.

(2) The wound-covering material according to item 1 wherein said moisture permeation-controlling layer is formed of a steam permeable resin film.

(3) The wound-covering material according to item 2 wherein said steam permeable resin film is a silicone elastomer film or a polyurethane elastomer film.

(4) The wound-covering material according to item 1 wherein said steam permeable resin film is a porous membrane of polyolefin and/or halogenated polyolefin, a surface of said porous membrane opposite to one which is in contact with said support layer being coated with a hydrophilic polymer by means of chemical bonding.

(5) The wound-covering material according to item 4 wherein said porous membrane is an elastic porous membrane.

(6) The wound-covering material according to item 1 wherein said biocompatible highly aqueous gel-forming substance is a member selected from the group consisting of carboxymethylcelluloses, alginates, hyaluronates, poly(meth)acrylates, chitosan derivatives and chitin derivatives.

(7) The wound-covering material according to item 1 wherein said biocompatible highly aqueous gel-forming substance contains carboxyl groups and a di- or higher valent metal bound to a plurality of the carboxyl groups.

(8) The wound-covering material according to item 7 wherein said metal is silver.

(9) The wound-covering material according to item 1 wherein said film of the highly aqueous gel-forming substance is a non-woven cloth, woven cloth, knitted cloth or a porous membrane.

(10) The wound-covering material according to item 1 wherein said water-repellent substance is a member selected from the group consisting of silicones, polyurethanes, styrene-butadiene-styrene block copolymers and polytetrafluoroethylenes.

(11) The wound-covering material according to item 1 wherein the water absorption capacity of said wound-covering material is 50–500% by weight.

(12) The wound-covering material according to item 1 wherein the steam permeability coefficient of said wound-covering material is 0.1–500 mg/cm$^2$/hr.

(13) A method for preparing wound-covering materials according to item 1 which comprises forming or preparing a film of a biocompatible highly aqueous gel-forming substance, contacting one surface of said film of the highly aqueous gel-forming substance with a solution containing a water-repellent substance and optionally an antimicrobial agent followed by drying, and mounting the other surface of said film of the highly aqueous gel-forming substance on a moisture permeable film-forming substance uncured and tacky but in film form and subsequently curing said moisture permeable film-forming substance.

Figure 1:
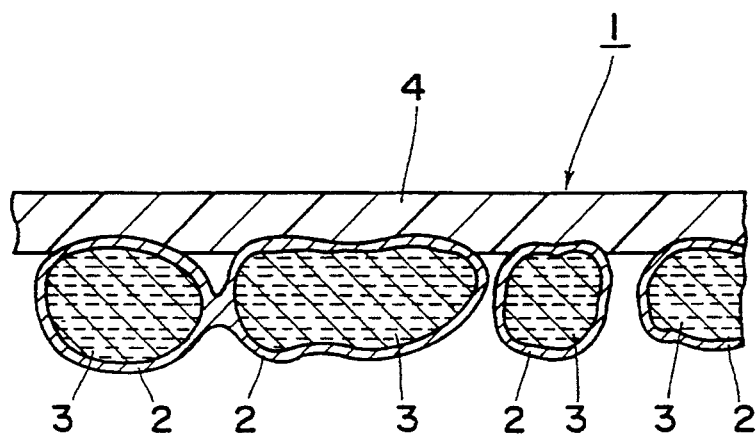
FIG. 1 is an enlarged sectional view showing fine structure of an embodiment of the wound-covering materials of the invention.

◯: Porous polypropylene membrane △: Porous polypropylene membrane graft polymerized with polymethoxyethyl acrylate ☐: Porous polypropylene membrane graft polymerized with polydimethylacrylamide.

DETAILED DESCRIPTION OF THE INVENTION

The wound-covering materials of the invention comprise two layers, a supporting layer to be contacted with a wound area and a layer of a moisture permeation-controlling layer and, optionally, either or both of said layers containing an antimicrobial agent.

The above-mentioned support layer formed of a biocompatible highly aqueous gel-forming substance is capable of retaining moisture and of absorbing water so that it has a function of adequately retaining exudate and maintains good contact with but no adhesion to the wound surface. These properties coupled with the inertness of the material to the tissues suppress pains. Consequently, proper biological environment created by a highly aqueous state is maintained, and healing, especially regeneration of the epidermis, is facilitated. Furthermore, close contact to the wound surface assures inhibition of the invasion of microorganisms into the wound surface.

The above-mentioned biocompatible highly aqueous gel-forming substance contains carboxyl groups and has a di- or higher valent metal bound to a plurality of carboxyl groups. Said metal preferably comprises antimicrobial activity The biocompatible highly aqueous gel-forming substance is preferably selected from the group consisting of carboxymethylcelluloses, alginates, hyaluronates, poly(meth)acrylates, chitosan derivatives and chitin derivatives. The film of the highly aqueous gel-forming substance is preferably a non-woven cloth, woven cloth, knitted cloth or a porous membrane. The above-mentioned water-repellent substance is preferably selected from the group consisting of silicones, polyurethanes, styrene-butadiene-styrene block copolymers and polytetrafluoroethylenes.

The moisture permeation-controlling layer preferably has steam permeability coefficient of 0.1–500 mg/cm$^2$/hr so that exudate does not stay under the support layer and wound does not dry.

Said moisture permeation-controlling layer is formed of a steam permeable resin film such as a silicone elastomer film or a polyurethane elastomer film.

Alternatively, the moisture permeation-controlling layer is formed of a porous membrane of polyolefin and/or halogenated polyolefin and a surface of said porous membrane opposite to the one which is in contact with said support layer is coated with a hydrophilic polymer by means of chemical bonding.

The porous membrane is composed of a polyolefin such as polyethylene or polypropylene or a halogenated polyolefin such as polyvinylidene fluoride, polyvinylidene chloride or chlorinated polyethylene or a mixture thereof.

The hydrophilic polymer with which the surface of the porous membrane is coated by means of chemical bonding may be any hydrophilic polymer. As preferable examples are mentioned polymethoxyethyl acrylate, polydimethylacrylamide, methoxy acrylic ester copolymers and dimethylacrylamide copolymers. Preferably, the porous membrane has a pore diameter of 0.01–1.0 μm and a steam permeation coefficient of 20–5000 g/m$^2$/24 hr according to JIS Z 0208 (ASTM F 372, ISO R 1195).

The elastic porous membrane is preferably a porous membrane provided with elasticity by graft polymerization with an acrylic ester, preferably ethyl acrylate or n-butyl acrylate, to the above-mentioned porous membrane. The graft polymerized porous membrane is preferably of a pore diameter in the range between 0.01 and 1.0 μm and a steam permeation coefficient in the range between 20–5000 g/m$^2$/24 hr. The instant wound-covering materials have a steam permeation coefficient of preferably 0.1–500 mg/cm$^2$/hr.

In the wound-covering materials of the present invention, antimicrobial agents can be contained in the support layer in order to sterilize bacterial infected wound area or to prevent the infection of bacteria.

The instant wound-covering materials can prevent infection from the outside because of the moisture permeation-controlling layer of the most outer layer. However, when the infection is severe requiring a large amount of an antimicrobial agent, the agent can be included in the moisture permeation-controlling layer.

As the antimicrobial comprised in the film of the highly aqueous gel-forming substance include sulfa drugs, antibiotics or the like. Given the nature of infections in wounded sites, those agents which have an antimicrobial spectrum including anti-*Staphylococcus* and anti-*Pseudomonas* activity are particularly similar.

The method for preparing the wound-covering materials according to the present invention is described below.

The wound-covering material is prepared first by forming or preparing a film of a biocompatible highly aqueous gel-forming substance, and contacting at least one surface of said film of the highly aqueous gel-forming substance with a solution of a water-repellent substance followed by drying. Then, the resulting film of the highly aqueous gel-forming substance is contacted with a solution containing ions of a divalent or higher metal followed by drying. The other surface of said film of the highly aqueous gel-forming substance is mounted on a moisture permeable film-forming substance uncured and tacky but in film form, and subsequently said moisture permeable film-forming substance is cured.

Specifically, a polymer such as a carboxymethylcellulose, an alginate, a hyaluronate, a poly(meth)acrylate, a chitosan or a chitin containing carboxyl groups on the side chain is formed into a film of a highly aqueous gel-forming substance in such a form as a non-woven cloth, woven cloth, knitted cloth or a porous membrane. The film of the highly aqueous gel-forming substance thus formed is contacted with a solution of a water-repellent substance such as a silicone, a polyurethane, a styrene-butadiene-styrene block copolymer or polytetrafluoroethylene in an appropriate solvent that does not dissolve the film of the highly aqueous gel-forming substance such as hexane, tetrahydrofuran or methyl ethyl ketone in a concentration of about 1–10% by weight by immersion, spraying or application by means of a roller or other tool followed by drying thereby applying the water-repellent substance at least partially to the surface of the film of the highly aqueous gel-forming substance to be in contact with a wound. The film of the highly aqueous gel-forming substance with the water-repellent substance attached thereon is contacted with a liquid containing about 0.1–5.0% by weight of ions of a di- or higher valent metal (for example, $Ca^{2+}$, $Zn^{2+}$, $Cu^{2+}$, $Al^{3+}$, $Ti^{4+}$) (such as an aqueous solution of calcium chloride, zinc chloride, zinc nitrate or copper nitrate) by immersion, spraying or application by means of a roller or other tool followed by drying. The process affords binding between the carboxyl groups of the film of the highly aqueous gel-forming substance and the metal ion to form a support layer.

Although the partial cross-linking treatment with metal ions may be conducted before coating with a water-repellent substance, the coating with a water-repellent substance is preferably carried out before the partial cross-linking in order to maintain the shape of the support layer.

A solution of a moisture permeable film-forming substance (for example, a substance to form a silicone elastomer or a polyurethane elastomer after curing) in an appropriate solvent such as hexane, tetrahydrofuran or methyl ethyl ketone in a concentration of about 50–70% by weight is applied to a plate-form base material by means of a precisely coating device (applicator). Immediately after the application (in tacky state before curing) is mounted the above-prepared support layer with the water-repellent substance attached and the divalent or higher valent metal introduced on the solution of the moisture permeable film-forming substance, which is then cured to complete preparation of the wound-covering substance of the invention. Silver is introduced into the support layer in order to produce wound-covering materials with higher antimicrobial activities. The highly aqueous gel-forming substance before or after the above-mentioned contact treatment with a liquid containing ions of a di- or higher valent metal is contacted with a liquid containing silver ions in a concentration of about 0.1–5.0% by weight (such as an aqueous solution of silver nitrate) thereby binding silver to a part of the carboxyl groups in the substance. Silver may be bound simultaneously with the di- or higher valent metal to the carboxyl groups of the highly aqueous gel-forming substance by adding a silver ion-containing liquid (such as an aqueous solution of silver nitrate) to a liquid containing a di- or higher valent metal.

Alternatively, the wound-covering materials can be prepared by laminating a hydrophylized porous membrane such as a polypropylene-membrane on a film of a biocompatible highly aqueous gel-forming substance partially coated with a water-repellent substance.

The hydrophylized polypropylene membrane can be prepared as follows.

Figure 2:
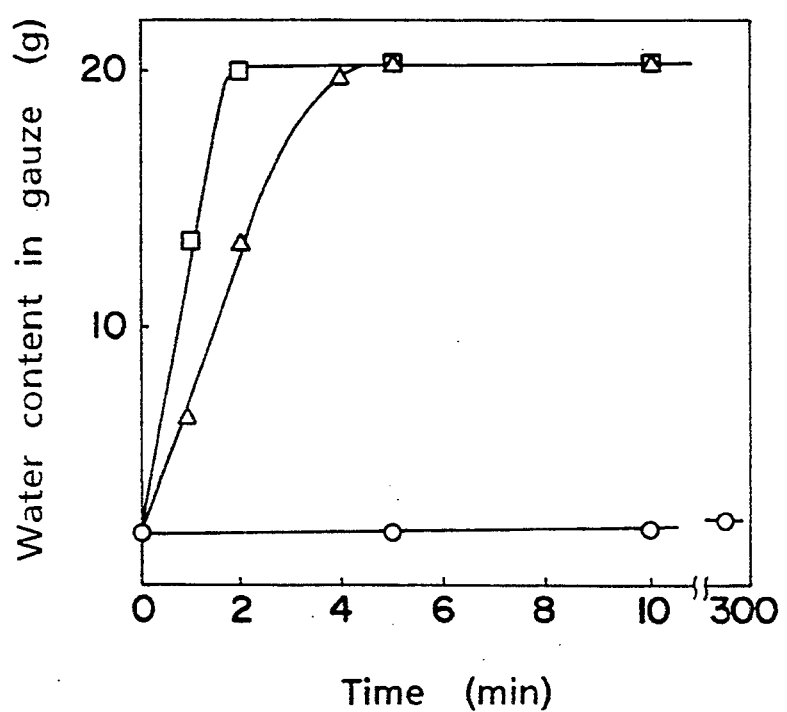
FIG. 2 shows changes of water content in the gauze piled on the cover material.

First, a predetermined amount of liquid paraffin and a crystalline nucleus-forming agent are added to powdery polypropylene, and the mixture is melt kneaded and formed into pellets. The pellets are molten at 150°–200° C., extruded in an extruder with T die and cooled to solidify to film. The liquid paraffin is extracted from said film, which is then subjected to heat treatment in air at around 135° C. for about 2 min. to prepare a porous polypropylene membrane. Said membrane is subjected to plasma-initiated surface graft polymerization with methoxyethyl acrylate to produce a hydrophilic porous polypropylene membrane. A porous polypropylene membrane can be made hydrophilic with dimethylpolyacrylamide in the same way as above. Results of a moisture permeation test for these membranes are shown in FIG. 2. Sponge in a dish was thoroughly impregnated with distilled water. On the surface of the sponge was mounted a cover material, on which gauze was piled. Then, the lid of the dish and a weight (approximately 5 g) were placed for pressure. The assembly was allowed to stand at room temperature and measured at predetermined time intervals for precise weight changes (Kazunori Ohara, Kiso to Rinsho (Basic and Clinical Medicine ) 16 (2) 617 (1982)). The wound-covering materials can be prepared by forming or preparing a film of a biocompatible highly aqueous gel-forming substance, contacting at least one surface of the film of the highly aqueous gel-forming substance with a water-repellent substance and a solution containing an antimicrobial agent, and then mounting on the other surface of the film of the highly aqueous gel-forming substance a porous polypropylene membrane which has been made hydrophilic.

The wound-covering material 1 of the invention will be described in detail with reference to an example as shown in FIG. 1.

The wound-covering material 1 of the example is made of the support layer 3 and the moisture permeation-controlling layer 4.

The support layer 3 is formed of a film of a biocompatible highly aqueous gel-forming substance. The use of a biocompatible substance is adopted in order that the wound-covering material 1 on covering wound will induce almost no foreign-matter reaction of the organism, has good affinity to the wound, especially to its surface and furthermore will not adhere to the wound surface with the exudate from the body.

As the biocompatible highly aqueous gel-forming substance may preferably be used macromolecular substances containing carboxyl groups on their side chain including carboxymethylcelluloses, alginates such as sodium alginate, hyaluronates such as sodium hyaluronate, poly(meth)acrylates such as sodium methacrylate, chitosan derivatives and chitin derivatives. In particular, non-woven cloth, woven cloth, knitted cloth or a porous membrane formed of such biocompatible highly aqueous gel-forming substance containing carboxyl groups on the macromolecular side chains are preferably employed. The support layer formed of a film of such biocompatible highly aqueous gel-forming substance is capable of absorbing and retaining water so that it has capability of adequately retaining the exudate and is capable of being in good contact with but no adhesion to the wound surface. The material, being of such properties and being biologically inert, exerts pain-inhibitory action. It follows that proper biological environment created by the highly aqueous state is maintained so that healing of the wound, especially regeneration of the epidermis is facilitated. Furthermore, the good contact with wound surface allows for protection of the wound surface from microbial invasion.

Moreover, in the wound-covering materials of the invention, ions of a di- or higher valent metal such as $Ca^{2+}$, $Zn^{2+}$, $Cu^{2+}$, $Al^{3+}$ or $Ti^{-4+}$ are bound to a plurality of the carboxyl groups contained in the highly aqueous gel-forming substance of the support layer 3 and partially coordinated or cross-linked. Formation of such partially cross-linked polymer makes the highly aqueous gel-forming substance so stable at the molecular level that decomposition and dissolution of the highly aqueous gel-forming substance in use are inhibited.

It is preferable that degree of the cross-linking with a di- or higher valent metal (proportion of the carboxyl groups bound to the di- or higher valent metal in all of the carboxyl groups present in the highly aqueous gel-forming substance) is about 50–100%. In a proportion of 50% or more, sufficient inhibition of decomposition and dissolution of the highly aqueous gel-forming substance in use can surely be accomplished. More preferably, the proportion is 75–100%. The di- or higher valent metal introduced into the support layer 3 is preferably Ca, Zn, Cu, Al, Ti or the like. The metal must not necessarily be one and may be more than one of the above-mentioned. It is preferable to employ Zn, Cu or the like in order to make the support layer 3, or finally the wound-covering material 1 antimicrobially active. For a broader antimicrobial spectrum, it is preferable to use a plurality of metal including Zn, Cu and the like.

It is also preferable to introduce silver into the highly aqueous gel-forming support layer (to bind silver to a part of the carboxyl groups) in order to have a wound-covering material with higher antimicrobial activities than those of Zn, Cu or the like. This enables inhibition of the growth of microorganisms in the wound and further infection with external microorganisms and promotes healing of the wound.

Moreover, of the support layer 3 formed of film of a highly aqueous gel-forming substance, at least a part of an area to be contacted with wound is coated with a water-repellent substance 2. Such coating with the water-repellent substance provides supplementation to the void contained in the support layer 3 formed of film of a highly aqueous gel-forming substance to serve as reinforcement or support to fraying or detachment of the support layer as well as to inhibit excessive absorption or to allow for adequate absorption of the exudate by the support layer. Coating of the support layer with a water-repellent substance also improves adhesion of such layer to the moisture-permeation controlling layer.

The water-repellent substance is preferably biocompatible. Such water-repellent substances includes silicones, potyurethanes, styrene-butadiene-styrene block copolymers, and polytetrafluoroethylenes. Particularly preferred are silicone elastomers and segmented polyurethanes.

It is preferable that the support layer coated with the water-repellent substance has a water absorption power of 50–500% by weight. More preferable is a water absorption power of 100–300% by weight.

On the side of the support layer 3 opposite to the area to be in contact with wound is formed a moisture permeation-controlling layer 4.

The moisture permeation-controlling layer 4 serves to maintain adequate retention of water thereby assuring a highly aqueous gelled state of the underlying support layer 3 and preventing external leakage of the protein components of the exudate while allowing steam to pass to provide a conducine environment for the repair of biotissues of the wound. The moisture permeation-controlling layer is formed of a steam permeable resin film. Illustrative is a film of a silicone elastomer, a polyurethane elastomer or the like. In addition, porous hydrophobic membranes (for example, porous polypropylene membrane and porous polyethylene membrane) with appropriate moisture permeability can preferably be used. Assuming that the support layer 3 per se is antibially active as described above, steam permeability coefficient of the moisture permeation-controlling layer 4 can be set in a wider range, being preferably 0.1–500 $mg/cm^2/hr$, more preferably 0.1–200 $mg/cm^2/hr$.

DESCRIPTION OF THE PREFERRED EMBODIMENTS

An example of the invention will be described in detail below with reference to the drawing.

EXAMPLE 1

A commercially available non-woven cloth made of sodium carboxymethylcellulose (manufactured by Asahi Kasei, a degree of etherification of 0.25) was immersed in a 5% solution of a medical grade Silastics ®-silicone (medical adhesive silicone type A, manufactured by Dow Corning) in hexane for 10 sec. and allowed to stand in a clean bench for drying. The non-woven cloth was then immersed in a 1% solution of calcium chloride for 10 sec., washed with water and allowed to stand in a clean bench for thorough drying. Then, the resulting non-woven cloth was mounted on a plate made of polytetrafluoroethylene which is sold under the trademark, Teflon, which had just been applied with a 67% solution of a medical grade Silastics ®-silicone (medical adhesive silicone type A, manufactured by Dow Corning) in hexane by means of a precisely coating device (applicator) to prepare a membrane. The treated non-woven cloth was allowed to stand at room temperature for 10 min. Subsequent curing in an oven at 60° C. for as little as one hour gave a wound-covering material according to the invention.

EXAMPLE 2

A commercially available non-woven cloth made of sodium carboxymethylcellulose (manufactured by Asahi Kasei, a degree of etherification of 0.25) was immersed in a 5% solution of a medical grade Silastics ®-silicone (medical adhesive silicone type A, manufactured by Dow Corning) in hexane for 10 sec. and allowed to stand in a clean bench for drying. The non-woven cloth was then immersed in a 1% solution of calcium chloride for 10 sec., washed with water and allowed to stand in a clean bench for drying. The resulting non-woven cloth was immersed in a 1% solution of silver nitrate ( ammoniacal ) for 30 sec., washed with water and allowed to stand in a clean bench for drying.

The non-woven cloth thus obtained was mounted on a Teflon plate which had just been applied with a 67% solution of a medical grade Silastics ®-silicone (medical adhesive silicone type A, manufactured by Dow Corning) in hexane by means of a precisely coating device (applicator) to prepare a membrane. The treated non-woven cloth was allowed to stand at room temperature for 10 min. Subsequent curing in an oven at 60° C. for as little as one hour gave a wound-covering material according to the invention.

COMPARATIVE EXAMPLE 1

A commercially available non-woven cloth made of sodium carboxymethylcellulose (manufactured by Asahi Kasei, a degree of etherification of 0.25) was immersed in a 1% solution of a medical grade Silastics ®-silicone (medical adhesive silicone type A, manufactured by Dow Corning) in hexane for 10 sec., and allowed to stand in a clean bench for drying. The non-woven cloth thus obtained was mounted on a Teflon plate which had just been applied with a 67% solution of a medical grade Silastics ®-silicone (medical adhesive silicone type A, manufactured by Dow Corning) in hexane by means of a precisely coating device (applicator) to prepare a membrane. The treated non-woven cloth was allowed to stand at room temperature for 10 min. Subsequent curing in an oven at 60° C. for as little as one hour gave a wound-covering material of the comparative example.

COMPARATIVE EXAMPLES 2-4

In Comparative Examples 2-4 were used a composite membrane made of a collagen-treated nylon mesh and a silicone membrane (Biobrane ® manufactured by Woodroof for Comparative Example 2), a chitin non-woven cloth (BESCHITIN-W ® manufactured by UNITIKA Ltd. for Comparative Example 3) and a collagen non-woven cloth (MEIPAC ® manufactured by Meiji Seika Kaisha, Ltd. for Comparative Example 4) all commercially available.

Experiments

Experiments were carried out using the wound-covering materials of Examples 1 and 2 and Comparative Examples 1-4 as follows.

Experiment 1: Assessment in animals

Japanese white rabbits (weighing 2.5-3.0 kg ) were shaved on the back, and then 4 wounds were formed on the back skin with a dermatome in a size of 2 cm × 2 cm and a depth of 5/100 in. On the wounds after hemostasis were placed the wound-covering materials of Examples 1 and 2 and Comparative Examples 1-4, each material for each wound. On the covered wound was further placed a non-adhesive covering material (Prima Pore ® manufactured by Smith & Nephew Inc. ), which was further covered with a flexible inside drape (Steri-Drape ® manufactured by 3M K. K.) and subsequently fixed with a flexible tape. The animals were fed water and feed ad lib. The animals were sacrificed under anesthesia 3, 7 and 14 days after the treatment, respectively. Assessments were made as follows.

(1) Percent cuticlarization

Two different sites of each wound were sampled three days after its preparation to prepare a tissue specimen. Optical microscopic pictures were successively taken at 18 magnifications. Length of the epidermis was measured and expressed in % of the length of the defective site.

(2) Thickness of the epidermis

Two different sites of each wound were sampled 14 days after its preparation to prepare a tissue specimen. While observing the tissue under optical microscope at 360 magnifications, length of the epidermis was measured for 5 sites.

(3) Detachment of the test materials (constituents of the wound-covering material)

Two different sites of each wound were sampled 3, 7 and 14 days after its preparation, respectively to prepare a tissue specimen. The tissue was subjected to histological examination for detachment and incorporation into the tissue of the test materials (constituents of the wound-covering material).

The assessment was rated on the following basis. —: No detachment, ±: Partially detached and incorporated into the epidermis, +: Entirely detached and incorporated into the pidermis, ++: Equivalent to +except for inhibition of cuticularization, +++: Incorporated into the dermis with inhibition of cuticularization.

(4) Tissue reaction

Two different sites of each wound were sampled 3, 7 and 14 days after its preparation, respectively to prepare a tissue specimen. The tissue was subjected to histological examination for inflammatory and foreign-matter reactions.

The assessment was rated on the following basis. —: No reaction, ±: Slight reaction, ++: Moderate reaction, +++: Severe reaction.

The results of the above assessments are shown in Table 1.

TABLE 1

| | Percent cuticularization (%) | Thickness of epidermis ($\mu$m) | Detachment of test material | Tissue reaction |
|---|---|---|---|---|
| Example 1 | 79.5 | 13.9 | ± | — |
| Example 2 | 78.0 | 14.0 | ± | ± |
| Comparative Example 1 | 71.0 | 15.8 | + | ± |
| Comparative Example 2 | 57.8 | 20.4 | ± | ± |
| Comparative Example 3 | 27.1 | 20.9 | + | + |
| Comparative Example 4 | 21.0 | 35.5 | +++ | ++ |

The above results demonstrate that the materials of Examples 1 and 2 possess good epidermis-regenerating and hypertrophy-preventing actions, and furthermore, are effective in inhibiting detachment of the test material (constituents of the wound-covering material) as well as in reducing tissue reactions.

Experiment 2: Antimicrobial test

On sterilized dishes was placed a solid medium (Müller-Hinton agar, MHA, manufactured by Difco) in a portion of 20 ml/dish to prepare plates. Precultures of *Pseudomonas aeruginosa, Escherichia coli, Staphylococcus aureus* and *Staphylococcus epidermidis*, respectively were uniformly smeared on the plates. Test samples were prepared by cutting a covering material of Example 2 and Comparative Example 1, respectively into a circular piece 1 cm in diameter, and three pieces of the test sample were placed on a plate. After upside down incubated at 37° C. for 18 hours, the presence or absence of the inhibition zone and growth of the organism on the contacted surface of the non-woven cloth were observed.

The results are shown in Table 2.

TABLE 2

|  | P. aeruginosa | E. coli | Staph. aureus | Staph. epidemidis |
|---|---|---|---|---|
| Example 2 | + | + | + | + |
| Comparative Example 1 | − | − | − | − |

The sign − in the table indicates no inhibition zone and growth of the organism on the contacted surface. The sign + indicates an inhibition zone observed. The above results demonstrate antimicrobial activities of the material according to Example 2.

EXAMPLE 3

A commercially available non-woven cloth made of sodium carboxymethylcellulose (manufactured by Tokai Senko K. K., degree of etherification of 0.40) was immersed in a hexane solution of 5% medical grade Silastics ®-silicone (medical adhesive silicone type A, manufactured by Dow Corning) with powdery silver sulfadiazine (AgSD) dispersed for 10 sec. and dried by allowing to stand in a clean bench. Then the non-woven cloth was immersed in a 1% solution of calcium chloride for 10 sec., washed with water and thoroughly dried by allowing to stand in a clean bench.

Separately, a hexane solution of 67% medical-grade Silastics ®-silicone (medical adhesive silicone type A, manufactured by Dow Corning) was applied to a Teflon plate using a precisely coating tool (applicator) to prepare a membrane. On the wet layer of the membrane immediately after the application was piled the above-prepared non-woven cloth, and the composite was allowed to stand at room temperature for 10 min. followed by curing in an oven at 60° C. for at least one hour. There was obtained a wound-covering material of the invention.

Experiment 3: Antimicrobial test

On sterilized dishes were placed a solid medium (Müller Hinton Agar, MHA manufactured by Difco) in a proportion of 20 ml/dish to prepare plates. On the plate was uniformly smeared a preculture of *Pseudomonas aeruginosa, Escherichia coli, Staphylococcus aureus* or *Staphylococcus epidermidis*. On the smeared plates were placed three pieces of the covering material cut into a circle 1 cm in diameter per solid medium plate. The plates were subjected to inversion culture at 37° C. for 18 hours, and then the presence or absence of the inhibitory zone and growth of the organism on the surface in contact with the non-woven cloth.

The results are shown in Table 3.

TABLE 3

| | Organism | | | |
|---|---|---|---|---|
| Sample | P. aeruginosa | E. coli | Staph. aureus | Staph. epidermidis |
| Control (CMC non-woven cloth only) | − | − | − | − |
| AgSD (1.4 mg/25 cm²) | ± | ± | ± | ± |
| AgSD (7.9 mg/25 cm²) | + | + | + | + |
| AgSD (6.3 mg/25 cm²) | + | + | + | + |

TABLE 3-continued

| | Organism | | | |
|---|---|---|---|---|
| Sample | P. aeruginosa | E. coli | Staph. aureus | Staph. epidermidis |
| AgSD (10.7 mg/25 cm²) | + | + | + | + |

(−: No inhibitory zone, ±: Inhibitory zone faintly formed (≦1 mm), +: Inhibitory zone formed (3-5 mm))

The sign − in the table indicates no formation of inhibitory zone and the sign + an inhibitory zone observed.

The antimicrobial effects were demonstrated by the above results.

EXAMPLE 4

Preparation of the porous membrane (1)

A mixture of polypropylenes having a melt flow index of 30 and 0.3, respectively (mixed weight ratio of 100:40) was melt kneaded with 400 parts by weight of liquid paraffin (average molecular weight of 324) and 0.3 part by weight of 1,3,2,4-bis(p-ethylbenzylidene)sorbitol crystalline nucleus-forming agent per 100 parts by weight of the polypropylene mixture, and the kneaded mass was pelleted using a twin-screw extruder. The pellets were molten in the same twin-screw extruder as above at 150°-200° C. and extruded through a T die with a slit of 0.6 mm into air to form filming. The filming was passed to a cooling and fixing solution by a guide roller placed just under the T die for cooling and fixing, and then wound-up. The wound-up filming was cut to a given size, longitudinally and transversely fixed and immersed in 1,1,2-trichloro-1,2,2-trifluoroethane four times each for 10 min. to extract the liquid paraffin in the filming. The resulting filming was then subjected to heat treatment in air at 135° C. for 2 min. to give a porous polypropylene membrane 0.6 μm in pore diameter and 140 μm in membrane thickness.

Preparation of the porous membrane (2)

A solution of 18 parts by weight of powdery polyvinylidene fluoride (Kynar K 301 manufactured by Mitsubishi Yuka K. K.) dissolved in 73.8 parts by weight of acetone and 8.2 parts by weight of dimethylformamide was cast onto a polyethylene terephthalate film and then immersed in a 1,1,2-trichlorotrifluoroethane bath for 5 min. followed by drying to give a porous polyvinylidene fluoride membrane 0.45 μm in pore size on average and 135 μm in membrane thickness.

Preparation of the elastic porous membrane (3)

The membrane obtained under (1) above was subjected to plasma-initiated surface graft polymerization with ethyl acrylate to give a porous polypropylene membrane provided with elasticity. Thus, the PP membrane was irradiated with argon plasma under 0.1 Torr for 15 sec. and then graft polymerized in the atmosphere of ethyl acrylate (25° C., 4 Torr) for 30 min. The ethyl acrylate-grafted PP membrane produced has an elongation at break of approximately 200%, which was not broken even when used at flexible parts such as joints in extremities.

Preparation of the elastic porous membrane (4)

The membrane obtained under (2) above was subjected to plasma-initiated surface graft polymerization with ethyl acrylate to give porous polyvinylidene fluoride membrane provided with elasticity.

Preparation of the porous membrane made hydrophilic (5)

The membranes obtained under (1)–(4) above were subjected to plasma-initiated surface graft polymerization with methoxyethyl acrylate to give a porous membrane made hydrophilic.

Preparation of the porous membrane made hydrophilic (6)

The membranes obtained under (1) and (3) above were subjected to plasma-initiated surface graft polymerization with dimethylacrylamide to give a porous membrane made hydrophilic.

Preparation of the wound-covering material

Commercially available non-woven cloth made of sodium carboxymethylcellulose (manufactured by Tokai Senko K. K., degree of etherification of 0.40) was immersed in a 5% hexane solution of medical grade Silastics ®-silicone (medical adhesive silicone type A, manufactured by Dow Corning) for 10 sec. and while wet, backed with one of the porbus polypropylene membranes prepared above. The products were dried to give a wound-covering material.

On the porous membranes obtained above was piled gauze, and water content of the gauze was measured at predetermined intervals of time. The results are shown in FIG. 2. FIG. 2 indicates that the porous membranes made hydrophilic have high water retentivity and are capable of maintaining wet state at a constant level.

What is claimed is:

1. A wound-covering material comprising (a) a support layer formed of a film of a biocompatible highly aqueous gel-forming substance, wherein at least a portion of the support layer which is to be in contact with a wound includes a coating of a water-repellent substance selected from the group consisting of silicones, polyurethanes, styrene-butadiene-styrene block copolymers, and polytetrafluoroethylenes, said coating surrounding the film of said support layer, and (b) a moisture permeation-controlling layer which is attached on and in contact with said support layer on the side opposite to the portion of the support layer which is to be contacted with a wound, wherein said moisture permeation-controlling layer is a porous membrane comprised of either polyolefin or halogenated polyolefin and the surface of said porous membrane which is opposite to the surface of said porous membrane which is in contact with said support layer is coated with a hydrophilic polymer by means of chemical bonding, and optionally, (c) either or both of said layers containing an antimicrobial agent.

* * * * *

UNITED STATES PATENT AND TRADEMARK OFFICE
CERTIFICATE OF CORRECTION

PATENT NO. : 5,395,305
DATED : March 7, 1995
INVENTOR(S) : Mikio KOIDE et al

It is certified that error appears in the above-indentified patent and that said Letters Patent is hereby corrected as shown below:

In Column 3, line 9, delete "absorption" and insert -- absorptive --.
In Column 3, line 62, after "activity", insert -- . --.
In Column 4, line 7, after "has", insert -- a --.
In Column 4, line 59, delete "similar" and insert -- suitable --.
In Column 7, line 67, delete "potyurethanes" and insert -- polyurethanes --.
In Column 8, line 15, delete "conducine" and insert -- conducive --.
In Column 13, line 19, delete "porbus" and insert -- porous --.

Signed and Sealed this

Eighteenth Day of July, 1995

Attest:

BRUCE LEHMAN

*Attesting Officer*       *Commissioner of Patents and Trademarks*